(12) United States Patent
Franzone et al.

(10) Patent No.: US 9,132,109 B2
(45) Date of Patent: Sep. 15, 2015

(54) USE OF NON-STEROIDAL ANTI-INFLAMMATORY DRUGS BY INHALATION IN THE TREATMENT OF ACUTE AND CHRONIC BRONCHITIS

(75) Inventors: Jose Sebastian Franzone, Turin (IT); Sebastiano Bianco, Milan (IT); Giuseppe Zuccari, Sant'Angelo Lodigiano (IT); Claudio Franco Omini, Bussero (IT)

(73) Assignee: MEDESTEA RESEARCH & PRODUCTION S.P.A., Colleretto Giacosa (Torino) (IT)

(*) Notice: Subject to any disclaimer, the term of this patent is extended or adjusted under 35 U.S.C. 154(b) by 1258 days.

(21) Appl. No.: 11/908,560

(22) PCT Filed: Mar. 10, 2006

(86) PCT No.: PCT/EP2006/002226
§ 371 (c)(1),
(2), (4) Date: Jul. 21, 2008

(87) PCT Pub. No.: WO2006/097247
PCT Pub. Date: Sep. 21, 2006

(65) Prior Publication Data
US 2008/0306033 A1    Dec. 11, 2008

(30) Foreign Application Priority Data
Mar. 15, 2005    (IT) .............................. MI2005A0417

(51) Int. Cl.
| A61K 31/19 | (2006.01) |
|---|---|
| A61K 31/192 | (2006.01) |
| A61K 31/21 | (2006.01) |
| A61K 31/235 | (2006.01) |
| A61K 31/196 | (2006.01) |
| A61K 31/542 | (2006.01) |
| A61K 31/60 | (2006.01) |

(52) U.S. Cl.
CPC ............... *A61K 31/196* (2013.01); *A61K 31/19* (2013.01); *A61K 31/192* (2013.01); *A61K 31/21* (2013.01); *A61K 31/235* (2013.01); *A61K 31/542* (2013.01); *A61K 31/60* (2013.01)

(58) Field of Classification Search
CPC ..... A61K 31/19; A61K 31/192; A61K 31/21; A61K 31/235
USPC ........................ 514/165, 226.5, 420, 570, 183
See application file for complete search history.

(56) References Cited

U.S. PATENT DOCUMENTS

| 5,883,084 A * | 3/1999 | Peterson et al. ................. 514/78 |
| 2002/0147216 A1 | 10/2002 | Zhou et al. |

FOREIGN PATENT DOCUMENTS

| EP | 0499143 | 2/1992 |
| WO | 2005018624 | 3/2005 |

OTHER PUBLICATIONS

STN Evidentiary Evidence Lysine Aspirin is Lysine Acetylsalicylate acid.pdf.*
Barberi, I_Drugs_01_02_199302_1993_46_Suppl_1_219-21.pdf.*
Tamaoki J et al., Effect of indomethacin on bronchorrhea in patients with chronic bronchitis, diffuse panbronchiolitis, or bronchiectasis, The American Review of Respiratory Disease, Mar. 1992, pp. 548-552.
Zavala Trujillo I et al, Potassium diclofenac as adjuvant in the treatment of acute bronchitis, Investigation Medica Internacional 1984, Mexico, vol. 11, No. 2, 1984, pp. 122-125.
Basili S et al., Potential usefulness of antiplatelet agents in patients with chronic obstructive pulmonary disease, Thrombosis Research Nov. 15, 1996, vol. 84, No. 4, Nov. 15, 1996, pp. 279-284.
Merk Research Laboratories; The Merk Index 13th Edition, 2001, Merk & Co. Inc., NJ, USA.
Jeffery P K, Structural and inflammatory changes in COPD: a comparison with asthma, Thorax. Feb. 1998, pp. 129-136.
Celli B R et al., Standards for diagnosis and treatment of patients with COPD: a summary of the ATS/ERS position paper, The European Respiratory Journal: Official Journal of the European Society for Clinical Respiratory Physiology, Jun. 2004, vol. 23, No. 6, pp. 932-946.
Mannino, David M., Chronic Obstructive Pulmonary Disease: Definition and Epidemiology, Respiratory Care, Dec. 2003, vol. 43, No. 12, pp. 1185-1193.
Martinez, FJ et al., Respiratory response to arm elevation in patients with chronic airflow obstruction; Am Rev Respir Dis., Mar. 1991, 143(3):476-80.
Openshaw, PJ et al., Observations on sputum production in patients with variable airflow obstruction; implications for the diagnosis of asthma and chronic bronchitis; Respir Med; Jan. 1989; 83(1):25-31.
Sestini, Piersante et al., Different Effects of Inhaled Aspirinlike Drugs on Allergen-Induced Early and Late Asthmatic Responses, Am J Respir Crit Care Med vol. 159, pp. 1228-1233, 1999, internet address www.atsjournals.org.
Holcroft, Christina A, et al., Measurement Characteristics of Peak Expiratory Flow, CHEST Official Publication of the American College of Chest Physicians, 2003, 124;501-510.
Hanania, Nicola A, et al., The Efficacy and Safety of Fluticasone Propionate (250ug)/Salmeterol (50ug) Combined in the Diskus Inhaler for the Treatment of COPD, CHEST Official Publication of the American College of Chest Physicians, 2003, 124;834-843.

* cited by examiner

*Primary Examiner* — Yong Chong
(74) *Attorney, Agent, or Firm* — Roylance, Abrams, Berdo & Goodman, L.L.P.

(57) ABSTRACT

A method for treating non-asthmatic bronchitis with a particular lysine acetylsalicylate is described. The lysine acetylsalicylate is delivered by nebulizer, preferably, to treat acute bronchitis, chronic bronchitis, emphysema and chronic obstructive pulmonary disease.

4 Claims, No Drawings

USE OF NON-STEROIDAL ANTI-INFLAMMATORY DRUGS BY INHALATION IN THE TREATMENT OF ACUTE AND CHRONIC BRONCHITIS

FIELD OF THE INVENTION

This invention relates to the use of non-steroidal anti-inflammatory drugs to prepare medicinal products designed to be administered by inhalation for the treatment of non-asthmatic bronchitis.

BACKGROUND OF THE INVENTION

Non-asthmatic obstructive pulmonary diseases, such as chronic obstructive pulmonary disease (COPD), are among the major causes of morbidity and mortality in Western countries, and this disease is expected to increase substantially in the coming decades. The two major risk factors for COPD are cigarette smoking and occupational exposure to chemical agents and dust, and atmospheric pollution in general.

The epidemiological data indicate that a very large number of patients suffer from the disease (9.34/1000 men and 7.33/1000 women), and the financial and social burden was estimated at 23,900 million dollars in 1993 in the USA alone. The importance of COPD, not only in scientific terms but above all from the socioeconomic standpoint, is also confirmed by the institution of an international project called GOLD (Global Initiative for Chronic Obstructive Lung Disease), which is designed to make the world's population aware of the risks deriving from COPD and to reduce the morbidity and mortality it entails. The project is sponsored by a number of public and private organisations, including the NHLBI and the WHO (www.goldcopd.com).

From the diagnostic standpoint, the definition of COPD is not universally agreed (D M Mannino. Resp. Care 2003; 48: 1185-93); however, it can be defined as a disease characterised by respiratory failure which is not fully reversible and remains unchanged for several months (P K Jeffery. Thorax 1998; 53: 129-36). A characteristic feature of COPD patients is the chronic presence of coughing and catarrh, although not all patients who exhibit these symptoms later develop COPD. However, the presence of coughing and bronchial hypersecretions for numerous days a year is very often a warning sign of COPD.

The airways of COPD patients also feature a marked presence of inflammatory processes, although the predominant cell phenotypes and anatomical location are different from those found in asthma, another pulmonary disease (P K Jeffery. Thorax 1998; 53: 129-36). Although there may be a marginal overlap of the two diseases in some patients, asthma and COPD are two distinct disorders, with very different guidelines for their diagnosis and pharmacological treatment (B R Celli et al. Eur. Respir. J. 2004; 932-46; Am. Thoracic Society. Am. Rev Respir. Dis. 1991; 152: S77-S121).

These guidelines, issued jointly by the ATS (American Thoracic Society) and ERS (European Respiratory Society), give precise information about the specific characteristics of the two diseases, allowing a differentiated diagnosis (B R Celli et al. Eur. Respir. J. 2004; 932-46), which is required to treat the disease effectively.

The distinctive signs of COPD are appearance in middle age, symptoms that progress slowly, a long personal history of smoking, abundant phlegm, and frequent flare-ups of infectious origin, whereas asthma is characterised by early onset, variable symptoms, which are present during the night or in the early morning, the presence of allergies, rhinitis or eczema, a family history of the disease, and largely reversible broncho-obstruction (B R Celli et al. Eur. Respir. J. 2004; 932-46).

As stated in the ATS/ERS guidelines, the medicinal products currently available reduce the symptoms, but as expressly indicated, "At present, no treatment has modified the rate of decline in lung function. The inhaled route is preferred" (B R Celli et al. Eur. Respir. J. 2004; p. 936).

There is consequently an evident need for new drugs to treat COPD, especially drugs which can be used by inhalation. Acetylsalicylic acid and other non-steroidal anti-inflammatory drugs (NSAIDs), administered by the inhalation route, are highly effective against asthma, as demonstrated by EP0499143B1.

SUMMARY OF THE INVENTION

Surprisingly, it has been found that the administration by inhalation of aspirin and other NSAIDs, especially tenoxicam, diclofenac and their salts, reduces the broncho-obstructive symptoms of COPD patients.

DETAILED DESCRIPTION OF THE INVENTION

"Inhalation route" means the administration through suitable devices, by mouth and nose, of solutions, suspensions and powders of active constituents, to which suitable excipients may be added.

The formulations are those classically employed by the inhalation route, requiring the use of piston-driven or ultrasonic nebulisers or any other nebuliser for the administration of solutions or suspensions suitable for aerosol therapy. Alternatively, pressurised canisters with suitable gases or gaseous liquids that deliver fractionated doses of the drug can be used. Suitable powder delivery devices can also be used.

This invention is entirely new and unexpected because, as already mentioned, although asthma and COPD both involve the respiratory apparatus, they are two wholly distinct diseases, which above all have entirely different aetiopathogenetic mechanisms (B R Celli et al. Eur. Respir. J. 2004; 932-46; P K Jeffery. Thorax 1998; 53: 129-36).

The latest asthma drugs, i.e. those which came into therapeutic use most recently, such as antileukotrienes, and previously nedocromil, are not currently recommended for the treatment of COPD (www.goldcopd.com Executive Summary revised Aug. 9, 2004; p. 15).

This invention is not even anticipated by the prior art relating to interference by aspirin with the production of sputum in bronchitis patients. In fact, Inoue H et al. (Fukuoka Igaku Zasshi. 1991; 82(4): 177-80) demonstrated that the administration of aspirin by inhalation reduces the sputum volume in bronchitic patients. This result was confirmed by Tamaoki J. et al. (Am Rev Respir Dis. 1992; 145: 548-52), using an indomethacin inhaler and once again evaluating the reduction in sputum volume of bronchitic patients. However, the same authors, citing an earlier study, state that pulmonary obstruction is not correlated with the volume of sputum produced by the patient (Openshaw P J M and Turner-Warwick M. Respir Med. 1989; 83: 25-31). Yet this invention surprisingly demonstrates that in bronchitic patients there is a definite improvement in the pulmonary function, with a reduction in the pulmonary pro-inflammatory parameters after administration of aspirin by nebuliser. In fact, as expressly stated by Tamaoki et al., in their study they did not observe any significant variation in respiratory function ($FEV_1$), and by their own admission, the difference in the sensation of effort perceived by the patients was mainly associated with changes in psychological factors (Borg's ratio scale). Further, the mechanism postulated by those authors, namely interference with cyclo-oxygenases, which is common to both drugs (indomethacin and aspirin) and other NSAIDs, could not be predictive of a favourable action by aspirin and other NSAIDs on the bronchopulmonary function parameters in chronic bronchitics. Sestini P. et al. (Am J Respir Crit Care Med. 1999; 159: 1228-33) recently reported that the administration of aspirin and indomethacin by inhalation generated opposite effects in bronchospasm induced by allergens in asthma patients: aspirin inhibited the immediate allergen-induced bronchoconstriction, while indomethacin was ineffective. This result led to the conclusion that the different activities of indomethacin and aspirin in broncho-constriction of allergic origin could not be connected with mere interference with the prostaglandin system.

EXAMPLE

The study involved 4 patients with a diagnosis of COPD according to the ATS/ERS guidelines (B R Celli et al. Eur. Respir. J. 2004; 23: 932-46), who were smokers or former smokers ($\geq 20$ packets a year). The patients were instructed in the use of a peak expiratory flow (PEF) measuring device using a peak flowmeter, and asked to record the PEF measurements in a daily diary. The measurements were performed 3 times a day: immediately after getting up in the morning, before lunch, and at night before going to bed. At least 3 daily PEF measurements are considered a good method for the measurement of pulmonary function (C A. Holcroft et al., Chest, 2003; 124: 501-10). PEF measurement has also been used, together with other spirometric tests, to evaluate potential COPD drugs (N A. Hanania et al., Chest, 2003; 124: 834-43). The patients were suitably instructed as to how to perform the PEF measurements, and asked to record the various measurements and any symptoms, whether correlated with the disease or not, in a daily diary. Before beginning treatment with 900 mg lysine acetylsalicylate (equivalent to 500 mg of acetylsalicylic acid) twice a day, morning and evening, administered after measurement of the corresponding PEF, the patients discontinued all pharmacological treatment except for short-acting bronchodilators in accordance with the ATS/ERS guidelines (B R Celli et al. Eur. Respir. J. 2004; 932-46) as first-line of treatment. This basic treatment was continued for 15 days, during which the PEF values were recorded; their mean value was considered as the baseline value. At the end of the 15 days' baseline treatment, the patients were treated with the drug by inhalation, as already mentioned, and this treatment was continued for the next 30 days. Sputum samples were taken at the beginning and end of the pharmacological treatment. Two patients who underwent treatment by inhalation with lysine acetylsalicylate presented a mean increase of approx. 8-10 L/min in PEF, and similar values at all 3 daily measurements. Similar results were obtained on 1 patient using diclofenac sodium at the dose of 75 mg twice a day, and on another with 20 mg of piroxicam twice a day.

It is evident from our findings that aspirin and other NSAIDs perform a definite therapeutic action in COPD, in view of the fact that these three drugs have entirely different structures although they all belong to the class of non-steroidal anti-inflammatory drugs; it can therefore be concluded that all the drugs belonging to that class perform a therapeutic role in COPD when administered by the inhalation route.

It is also interesting to note that administration of NSAIDs by nebuliser was active not only in favourably modifying patients' expectorate during and after pharmacological treatment, but also in the treatment of patients with acute bronchitis, chronic bronchitis and emphysema.

As the preferred administration route for NSAIDs in the treatment of non-asthmatic bronchitis is the inhalation route, the preferred pharmaceutical formulations are all those which can be used by inhalation, especially those which allow better deposit and absorption of the drug in the lung structures involved in the disease, such as the bronchi and bronchioles, the lung parenchyma, and all cells, fluids and anatomical structures contained in them.

The invention claimed is:

1. A method for the treatment of chronic bronchitis, chronic obstructive pulmonary disease in adults, and emphysema comprising administering by inhalation medicinal products including a lysine salt of acetylsalicylic acid.

2. The method according to claim 1, wherein the lysine salt of acetylsalicylic acid is administered in an amount sufficient to increase pulmonary function of a patient.

3. A method of administering to adults a lysine salt of acetylsalicylic acid in a medicinal product for administration comprising inhaling the lysine salt of acetylsalicylic acid for treatment of chronic bronchitis, chronic obstructive pulmonary disease, and emphysema.

4. The method according to claim 3, wherein the lysine salt of acetylsalicylic acid is administered in an amount sufficient to increase pulmonary function of a patient.

* * * * *